Figure 1:
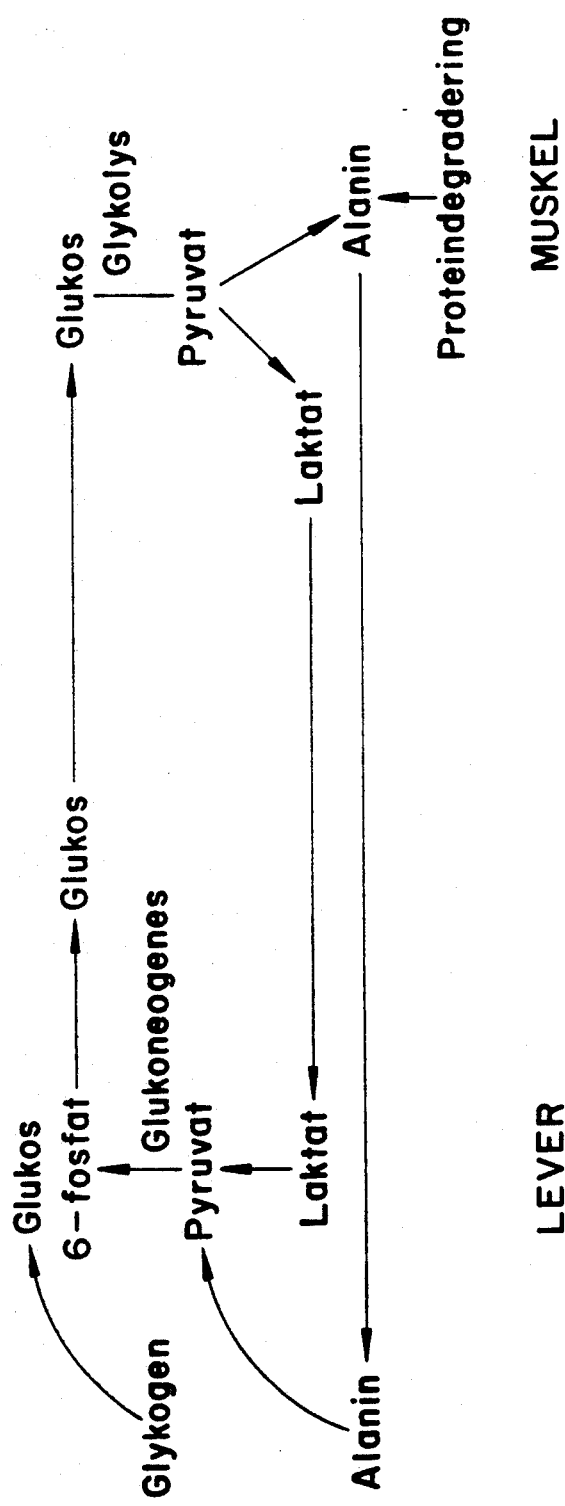

United States Patent [19]

Olin

[11] Patent Number: 5,183,674
[45] Date of Patent: Feb. 2, 1993

[54] FOOD AND FEEDSTUFF

[76] Inventor: Thomas Olin, Enbacken 33, S-183 46 Täby, Sweden

[21] Appl. No.: 678,972
[22] PCT Filed: Dec. 1, 1989
[86] PCT No.: PCT/SE89/00707
§ 371 Date: Apr. 25, 1991
§ 102(e) Date: Apr. 25, 1991
[87] PCT Pub. No.: WO90/06064
PCT Pub. Date: Jun. 14, 1990

[30] Foreign Application Priority Data

Dec. 2, 1988 [SE] Sweden .................. 8804376

[51] Int. Cl.$^5$ ............................................. A23K 1/00
[52] U.S. Cl. ............................ 426/2; 426/69; 426/656; 426/807; 514/557
[58] Field of Search ............... 426/69, 2, 656, 807; 514/419, 400, 557

[56] References Cited

U.S. PATENT DOCUMENTS

| | | | |
|---|---|---|---|
| 4,100,160 | 7/1978 | Walser | 514/400 |
| 4,100,161 | 7/1978 | Walser | 514/519 |
| 4,100,293 | 7/1978 | Walser | 424/317 |
| 4,744,990 | 5/1988 | Bragdon et al. | 426/2 |
| 4,871,552 | 10/1989 | Bragdon et al. | 426/2 |

OTHER PUBLICATIONS

The Merck Index Published by Merck & Co. 1968, Eighth Edition, pp. 600 and 897.
Routh, et al. *A Brief Introduction To General Organic And Biochemistry,* 1971, W. B. Saunders Company, Philadelphia, p. 400.

*Primary Examiner*—R. B. Penland
*Attorney, Agent, or Firm*—Burns, Doane, Swecker & Mathis

[57] ABSTRACT

The present invention relates to a process for reducing the excretion of nitrogen from humans and animals while maintaining formation of proteins, as well as a food and feedstuff for humans and animals comprising keto acids, whereby ingoing protein is replaced by alpha ketoglutaric acid; a combination of alpha keto glutaric acid and pyruvic acid; oxaloacetate or oxaloacetate in combination with alpha keto glutaric acid or pyruvate or another keto acid according to the formula R—CO—COOX, wherein R denotes a part of a nonessential amino acid and X denotes hydrogen, alkali metal, alkaline earth metal or organic base or non-toxic precursors or intermediates of these, whereby the keto acid (-s) is (are) present in an amount of 1 to 20% by weight, preferably 1–10% by weight of the protein dry matter present.

23 Claims, 5 Drawing Sheets

FOOD AND FEEDSTUFF

TECHNICAL FIELD

The present invention relates to a food and feedstuff for humans and animals comprising keto acids.

The object of the present invention is to obtain a food and feedstuff, which having a reduced content of proteins still might fulfil the demand of the animals as to access to protein forming and energy providing substances. Furthermore, the feedstuff shall fulfil the demand for access to biomolecules deriving from non-essential amino acids. The invention further aims to reduce the excretion of nitrogen from the organism.

BACKGROUND OF THE INVENTION

It is well known that water living carnivores, such as salmon, and land based carnivores, such as mink, live under natural conditions, on a diet consisting of 30 to 55% of proteins (90% DS). The choice of food is depending on live phase and specie. A great deal of this protein can be oxidized to form energy providing compounds, such as ATP (adenosine triphosphate), which results in excretion of nitrogen to the environment. At an intense cultivation of e.g. fish and mink this might cause an environmental problem.

During natural conditions omnivores live on a diet consisting of 15 to 30% of proteins (90% DS). During certain conditions this protein might be used for providing energy.

The most energy demanding tissue in the body is the muscles, which obtains its carbohydrate energy from the food directly via the blood or from the liver via the blood in the form of glucose. Glucose is formed in the liver from inter alia decomponents of the proteins of the muscles. The compounds which hereby form glucose are substantially alanine and its corresponding keto acid. It has also been shown that the corresponding keto acids of some essential amino acids, such as alpha keto isocaproate (KIC), may be precursors of amino acids, e.g. KIC of leucine.

Figure 5:
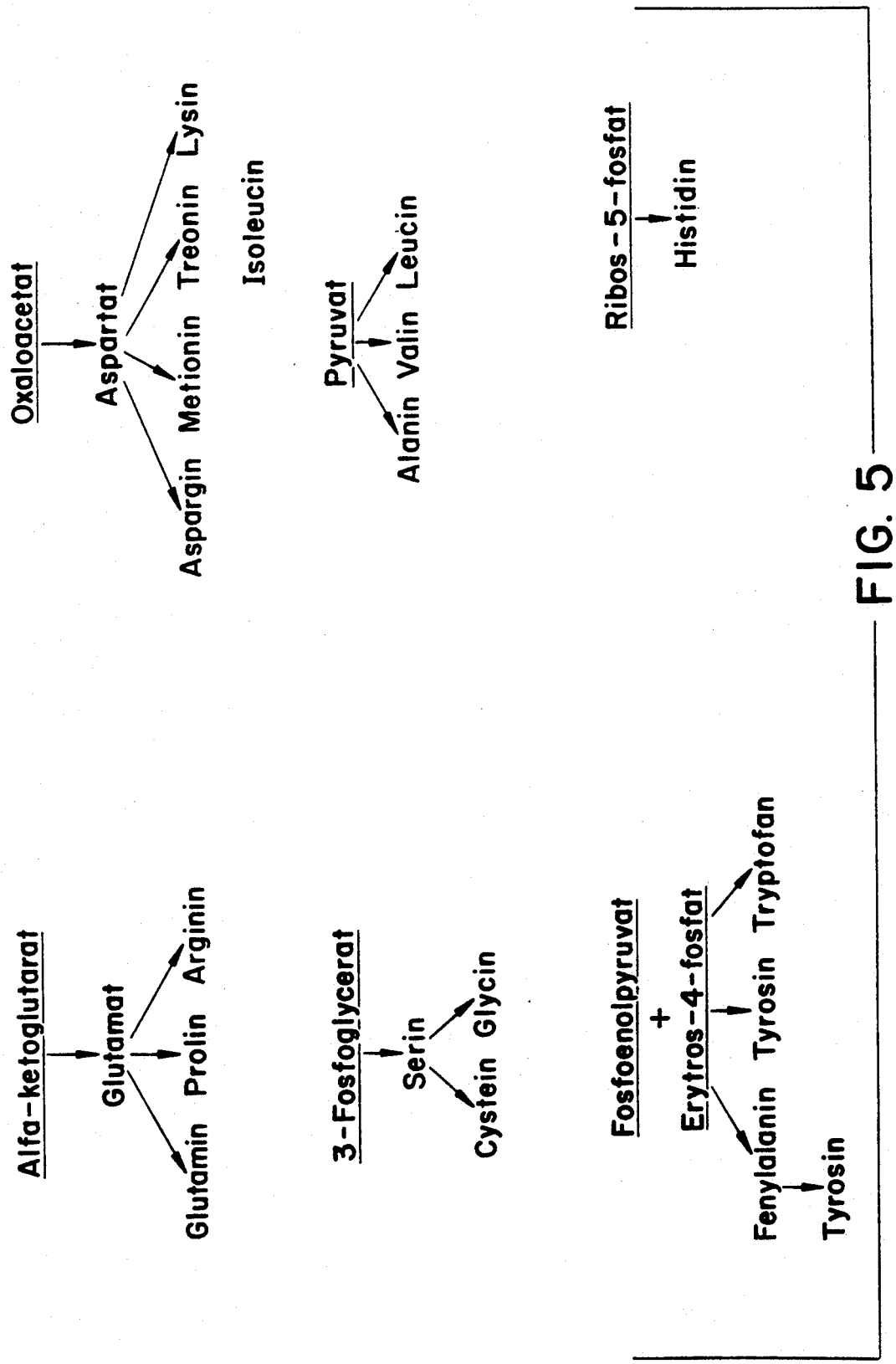

(i) $NH_4^+$ is coupled to amino acids via the reaction 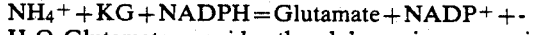
$NH_4^+ + KG + NADPH = Glutamate + NADP^+ + H_2O$ Glutamate provides the alpha amino group in the synthesis of most non-essential amino acids;

(ii) the carbon skeletons present in the synthesis of non-essential amino acids are all intermediates of the glucolysis, the pentose-monophosphate shunt or the citric acid cycle and may hereby be derived from pyruvate or KG (cf FIG. 5)

Figure 6:
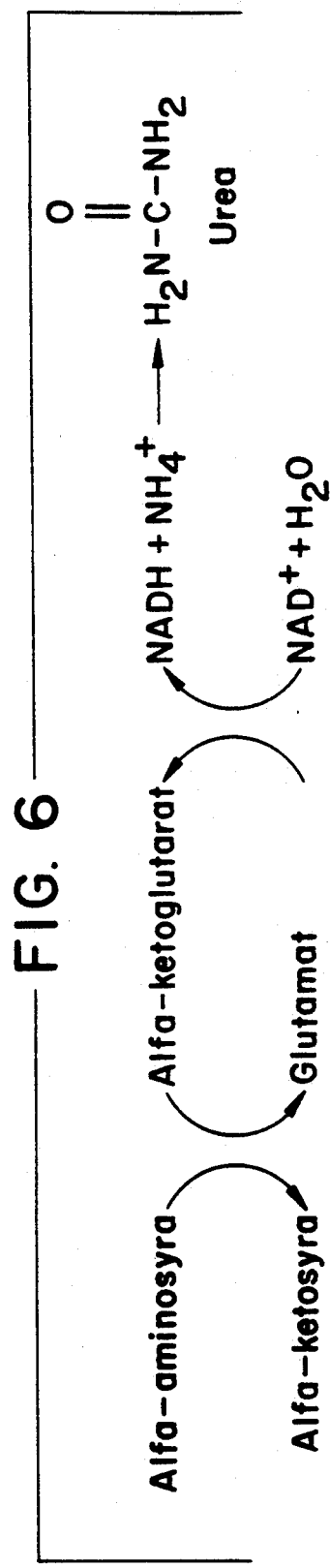
Figure 2:
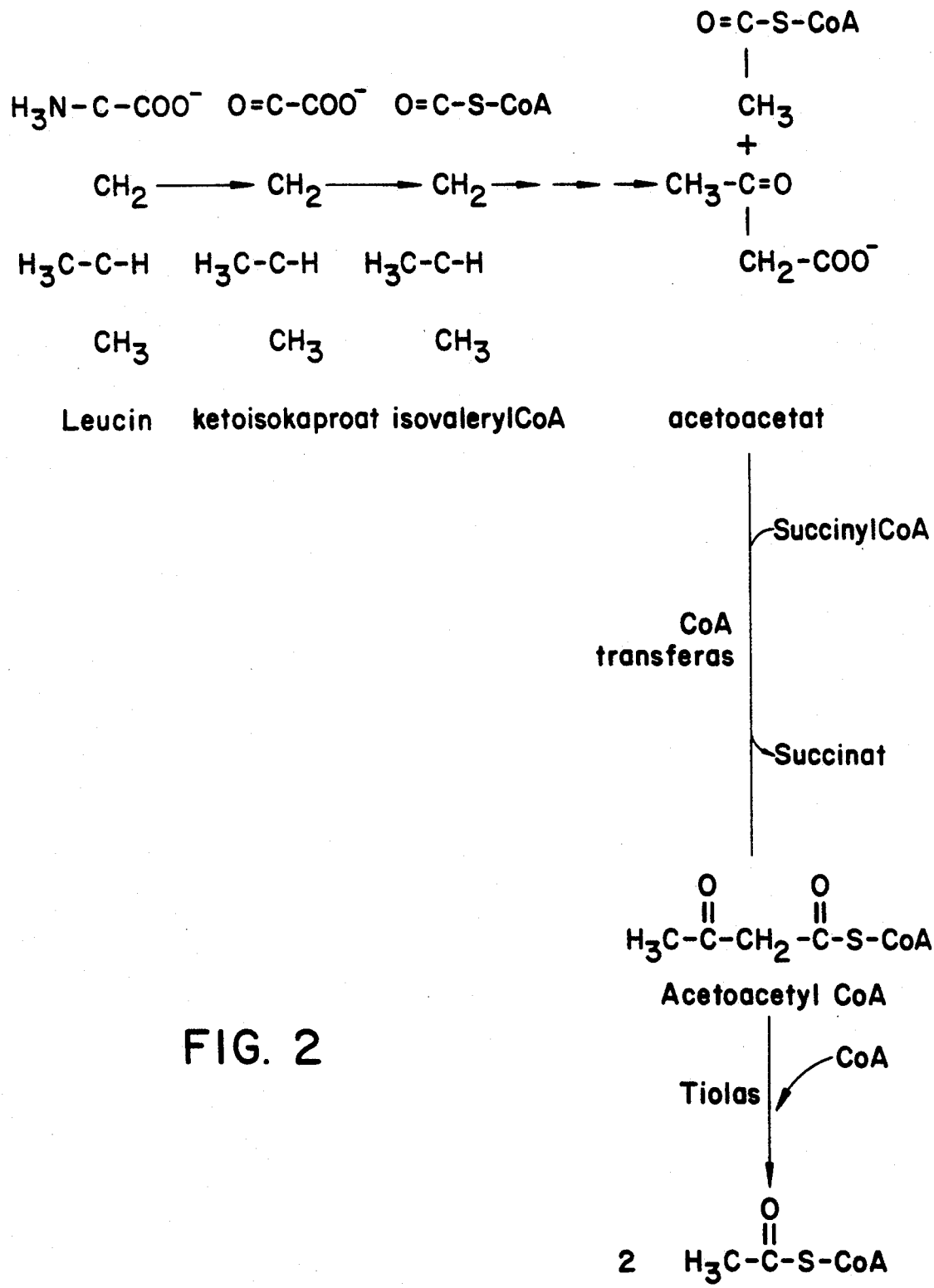
Figure 3:
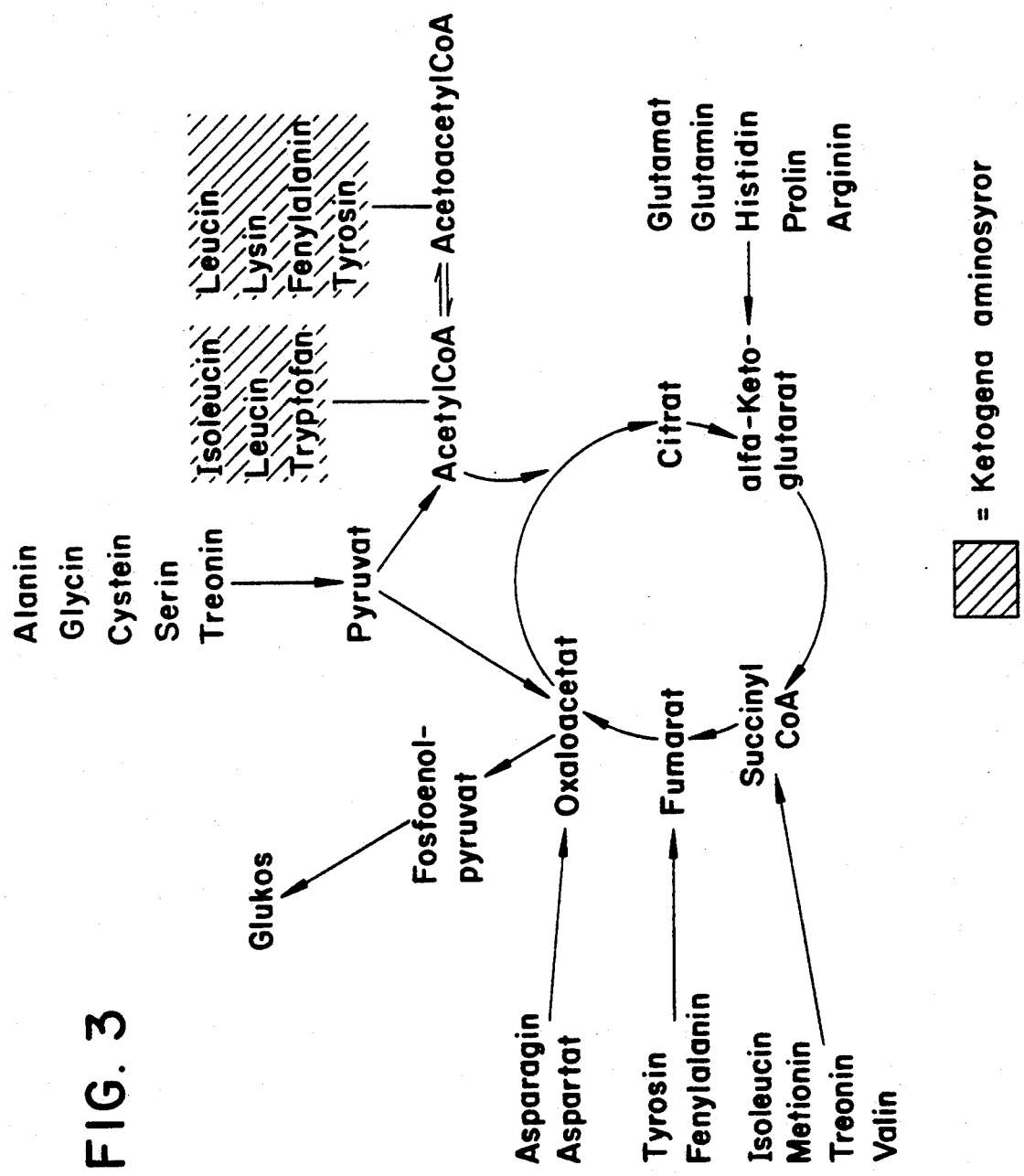

(iii) at physiological stress, too large energy draft, reproduction conditions and other low energy situations, the oxidation of amino acids increases whereby a deamination with KG or PY as amino receptors belongs to the starting processes (cf. FIG. 6);

(iv) at the synthesis of collagen KG is essential to the hydroxylation of proline.

Figure 4:
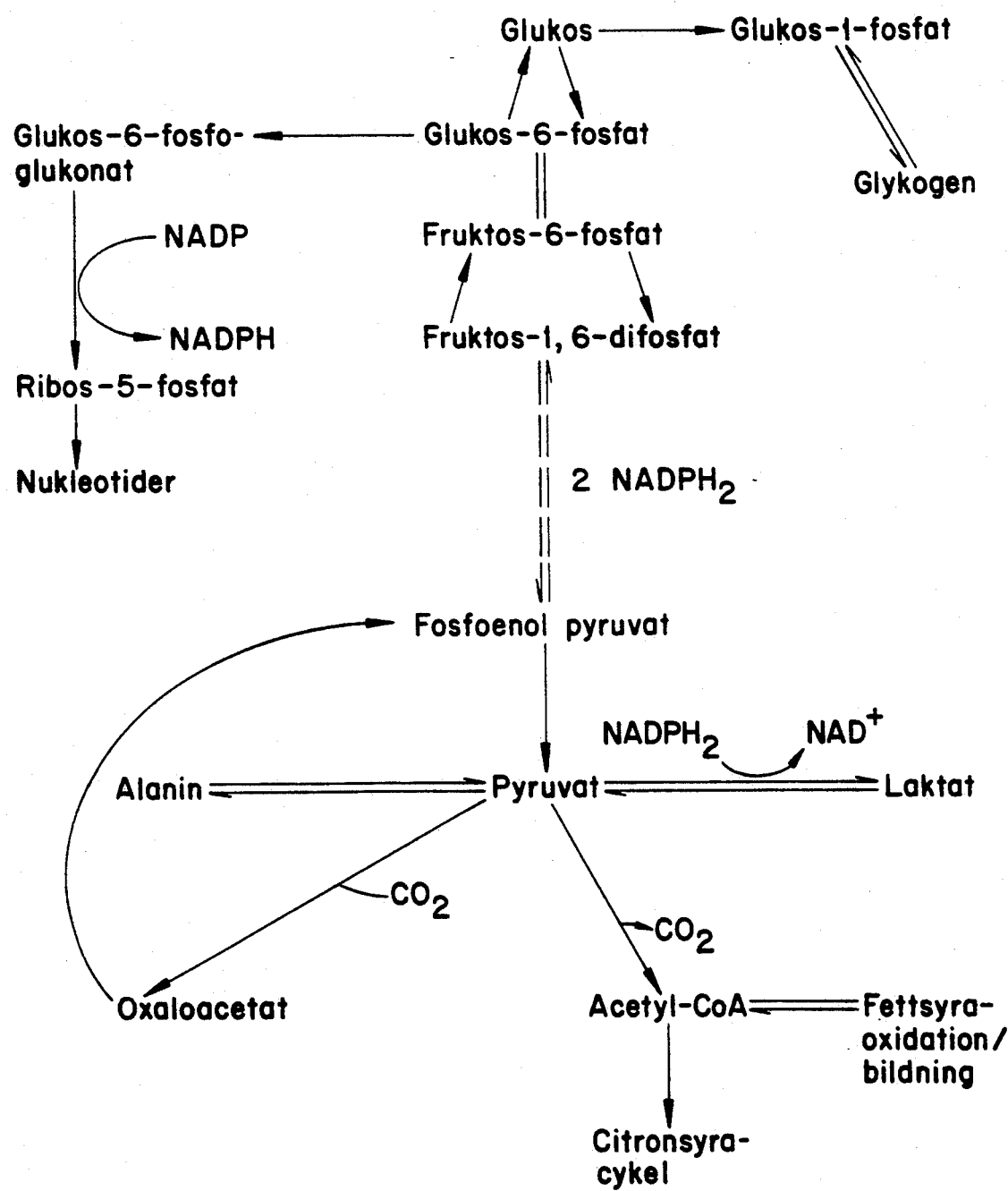

Pyruvate is a centre of the metabolism (cf. FIG. 4), where the following steps can be distinguished:

(i) the formation of lactate to provide the glucolysis with $NAD^+$ during aerobic conditions;

(ii) formation of acetyl-CoA for the synthesis of fatty acids or digestion in the citric acid cycle;

(iii) a high concentration of acetyl-CoA increases the formation of oxaloacetate, which either provides the citric acid cycle with intermediates (at a low concentration of ATP (adenosine triphosphate) or becomes a substrate in the gluconeogenesis (at high ATP concentrations);

(iv) at the gluconeogenesis pyruvate might possibly contribute to the pentose-monophosphate shunt, where NADPH is formed (essential in several anabolic processes, i.a. the synthesis of the non-essential amino acids) and ribose-5-phosphate, which is a substrate at the synthesis of nucleotides;

(v) the formation of alanine as well as other non-essential amino acids where pyruvate contributes with the carbon skeleton.

DESCRIPTION OF THE PRESENT INVENTION

It has now surprisingly been shown possible, with a maintained formation of proteins, to be able to reduce the excretion of nitrogen from animals and man by replacing a part of the protein of food and feedstuffs by means of the present invention. This is characterized in that the ingoing protein is replaced by alpha keto glutaric acid; a combination of alpha keto glutaric acid and pyruvic acid; oxaloacetate or oxaloacetate in combination with alpha keto glutaric acid or pyruvate or another keto acid according to the formula R—CO—COOX, wherein R denotes a part of a non-essential amino acid and X denotes hydrogen, alkali metal, alkaline earth metal or organic base or non-toxic precursors or intermediates of these.

The keto acids above can generally be defined by the formula R—CO—COOX, wherein R denotes a part of a non-essential amino acid and X denotes hydrogen, alkali metal, alkaline earth metal or organic base or non-toxic precursors or intermediates of such keto acids. These compounds will in the following for the reason of simplicity be called keto acids. These keto acids are present in an amount of 1 to 20% by weight, preferably 1 to 10% by weight, of the dry substance of the ingoing proteins.

Further characteristics will be evident from the accompanying claims.

Administration can be made to carnivores, omnivores and herbivores to reduce, in applicable cases, the excretion of nitrogen but also to achieve a protein saving effect.

By means of the present invention thus substrate in the form of keto acids of non-essential amino acids is supplied for the formation of proteins or other biomolecules deriving from these amino acids. The keto acids, which can metabolize, during aerobic conditions, in the mitochondria of the cells, give raise to energy providing and reducing compounds. Both these types of compounds are essential in active life processes. In the mitochondria intermediates are formed during the metabolism of keto acids, i.a. succinyl-CoA. Succinyl-CoA is present in the synthesis of the porfyrine molecule in haemoglobin and myoglobin. When keto acids are added to the organism a protein saving effect is obtained as the organism can use keto acids for non-essential amino acids in stead of using amino acids for other purposes than the formation of protein. Thereby the efficiency of the protein added increases. KG, one of the above described keto acids has a central position in the binding of $NH_4^+$ and later in the synthesis of non-essential amino acids. Different keto acids of non-essential amino acids are furthermore a more effective substrate than the amino acids themselves as no deamination needs to take place and the energy demanding excretion of nitrogen from the organism decreases. As evident from the Example 1 below, where fish spawns having obtained a feedstuff being supplemented with 10% keto acids, reduces the excretion of nitrogen with more than 20%.

The present invention can also be used for parenteral nutrition at catabolic situations, e.g. at large trauma, such as burn damages etc. but also at kidney damages.

During the reproductive phase when the fish mainly utilizes its muscle proteins added keto acids in stead be utilized, e.g. pyruvate, optionally in combination with KG. In that way the otherwise great loss of muscle protein can be reduced. Furthermore, the excretion of nitrogen is reduced.

The present invention will in the following be described more in detail with reference to the Examples given, however, without being restricted thereto.

EXAMPLE 1

Growth test.

1-summer spawns of salmon were fed during 5 weeks with partly a control feedstuff intended for very young salmon, partly a feedstuff according to the present invention based upon the same raw materials as the control feedstuff but moreover containing 5% of pyruvate Na-salt, and 5% alpha keto glutaric acid (KG), whereby 10% of the protein in the form of fish meal present in the control feedstuff had been replaced by keto acids. The test was carried out in such a way that 500 spawns in one trough obtained the control feedstuff and 500 spawns in another trough obtained a feedstuff according to the present invention. The spawn of salmon had an average weight of about 4 g each at the beginning of the test. Growth, nitrogen excre-tion, total analysis and protein analysis were carried out. Macroscopic investigation of the spawns was carried out as well.

| Composition of the feedstuff | Control | Test feedstuff |
|---|---|---|
| Vitamin and mineral premix | 2.0% | 2.0% |
| Binding agent, lignosulphate | 2.0% | 2.0% |
| Wheat, boiled in an autoclave | 18.8% | 18.8% |
| Soya, finely ground | 4.0% | 4.0% |
| Blood meal | 2.0% | 2.0% |
| Fish meal, whole meal | 63.2% | 53.2% |
| Lodda oil, lecithin | 10.0% | 10.0% |
| Alpha keto glutaric acid | — | 5.0% |
| Na-pyruvate | — | 5.0% |
| Total | 100.0% | 100.0% |

| Feedstuff analysis | Control | Test feedstuff |
|---|---|---|
| N-content | 9.46% | 7.90% |
| Cysteine | 5.8 g/kg | 4.7 g/kg |
| Methionine | 17.0 | 13.5 |
| Asparginic acid | 56.6 | 44.9 |
| Threonine | 25.2 | 20.4 |
| Serine | 26.2 | 21.0 |
| Glutamic acid | 89.8 | 75.2 |
| Proline | 27.4 | 21.0 |
| Glycine | 36.8 | 28.3 |
| Alanine | 38.1 | 30.4 |
| Valine | 33.6 | 27.0 |
| Isoleucine | 26.0 | 20.4 |
| Leucine | 46.3 | 37.1 |
| Tyrosine | 19.5 | 15.3 |
| Phenyl alanine | 24.2 | 20.0 |
| Histidine | 14.7 | 12.0 |
| Lysine | 43.9 | 34.3 |
| Arginine | 34.5 | 27.6 |
| Hydroxyproline | 7.5 | 3.7 |
| Sum | 572.9 | 456.9 |
| Ammonia | 9.0 | 7.2 |

| Feedstuff analysis | Control | Test feedstuff |
|---|---|---|
| Total | 581.9 | 464.1 |

The keto acids of the test feedstuff thus were 10% of the feedstuff and substituted 20% of the amino acids and thus reduced the nitrogen content with about 16%. Amino acid analysis of the feedstuff and the fish are carried out in accordance with official EEC-method.

| Analysis, spawns 100% DS | Control | Test feedstuff |
|---|---|---|
| N-content | 8.85% | 8.86% |
| Cysteine | 6.1 g/kg | 5.8 g/kg |
| Methionine | 17.7 | 15.5 |
| Asparginic acid | 53.8 | 51.1 |
| Threonine | 24.3 | 22.9 |
| Serine | 23.7 | 22.5 |
| Glutamic acid | 87.3 | 84.7 |
| Proline | 23.5 | 23.0 |
| Glycine | 38.6 | 38.1 |
| Alanine | 35.7 | 34.2 |
| Valine | 38.9 | 27.7 |
| Isoleucine | 23.2 | 23.2 |
| Leucine | 41.0 | 39.5 |
| Tyrosine | 18.5 | 17.9 |
| Phenyl alanine | 24.2 | 23.2 |
| Histidine | 13.2 | 12.8 |
| Lysine | 43.9 | 43.5 |
| Arginine | 32.4 | 32.0 |
| Sum | 534.7 | 517.4 |
| Ammonia | 8.2 | 7.3 |
| Total | 542.9 | 524.7 |

The results are mean values of three analyses based on 50 spawns each. The differences between the groups are non-significant.

Nitrogen excretion tests

In order to determine the excretion of nitrogen 10 spawns of each group were allowed to live in a closed trough filled with oxygenised water. The spawns lived in this environment during 90 minutes, whereupon they were killed, weighed and dissected. All spawns had their stomachs as well as intestines well filled with feedstuff. The excretion of $NH_3$ and $NH_4^+$ were analysed in water samples from the two troughs in such a way that the time differences between feeding, killing and final sampling was uniform. Ammonia was analysed in accordance with Parsons et al, A manual of Cheicaland Biological Methods for Seawater Analysis, Pergamon Press, pages 15–16 (ISBN-0-08-030288-2). The test which was carried out as a final of an earlier growth test was carried out when the fishes were about 20 weeks of age. No difference in mortality between control and test group could be noted during the added test periods.

| | Results | |
|---|---|---|
| Group of fishes | Weight (g + SEM) | Excretion of nitrogen ($\mu g\ NH_4^+/g\ BW^{-1} \times 1\ hr^{-1}$) |
| Control feedstuff | 3.75 ± 0.15 | 8.00 ± 0.69 |
| Test feedstuff | 3.77 ± 0.21 | 5.71 ± 0.37 |

The difference in excretion of nitrogen between the test groups is 28% and statistical significance in accordance with students t-test is $n=20$, $p \leq 0.01$.

Macroscopic analysis of the spawns.

Dissection of the spawns showed no difference between the groups with regard to liver status, stomach-intestinal filling and accumulation of visceral fat.

The spawns of the control group had at the beginning of the test an average weight of 3.40 g and at the end of the test an average weight of 3.95 g, while the group fed a feedstuff according to the present invention had an average weight of 3.56 g at the beginning of the test, and 4.11 g at the end of the test. The growth was thus equal.

EXAMPLE 2

In a test using recently veined rats according to Eggum (Eggum, B.O.; A Study of Certain Factors Influencing Protein Utilization in Rats and Pigs, National Institute of Animal Science, (1973), p.406) where a control feedstuff consisting of cereals, other carbohydrates, fish protein, fat, mineral, and vitamins was compared with a test feedstuff where 0.6% by weight of pyruvate and 0.8% by weight of alfa-ketoglutarate was allowed to replace 1.4% by weight of fish protein and where 0.15% by weight of soya oil was added to the test feedstuff in order to compensate for the difference in fat content appearing by the reduced content of fish protein, the following results were obtained:

TABLE 1

|  | Control group | Test group |
|---|---|---|
| Fecal digestibility (TD), % | 91.2 (1.6) | 92.4 (1.0) |
| Biological value (BV), % | 92.8 (1.1) | 94.6 (0.5) |
| Net protein utilization (NPU), % | 84.7* (1.9) | 87.4* (0.7) |
| Growth, grams | 13.8 (2.3) | 13.6 (1.7) |
| Protein of feedstuff, % DS | 10.39 | 9.16 |

Standard deviation within parenthesis
*Significant difference according to Student's t-test $p < 0.02$ The test, which was carried out in such a way that the total amount of feedstuff (g DS) was equal to the two groups of animals, showed no significant growth differences in spite of the fact that 1.4% by weight of the protein in the control feedstuff had been replaced by keto acids.

The net protein utilization which shows the animals' possibility of utilizing the protein added for building up a protein of its own shows as evident from Table 1, significant differences, mainly depending on better biological value (BV) of the test group. The protein improving effect is explained by the addition of, in this case, a combination of alfa-keto glutarate and pyruvate.

Macroscopical investigations of liver, kidneys, and other internal organs showed, moreover, no differences between the groups of animals.

At a composition of a feedstuff according to the present invention where large parts of the protein have been replaced by keto acids in accordance with above, the amount of salt should be restricted in order to avoid electrolytical disturbances. Thus other salts than sodium salts of the keto acids might be present, such as potassium, magnesium, and calcium salts. Free acids may be used as well.

I claim:

1. A process for reducing the excretion of nitrogen from humans or animals while maintaining protein formation, said process comprising administering to said humans or animals food and/or feedstuff wherein protein from said food and feedstuff has been replaced by at least one keto acid of a non-essential amino acid according to the formula R—CO—COOX, wherein R is a part of a non-essential amino acid and X is selected from the group consisting of hydrogen, an alkali metal, an alkaline earth metal or an organic base, wherein said keto acid is present in an amount of 1 to 20% by weight of the protein dry matter present and wherein nitrogen excretion is substantially reduced.

2. The process of claim 1, wherein said keto acid is selected from alpha ketoglutaric acid, pyruvic acid, and oxaloacetate.

3. The process of claim 1, wherein said keto acid is present in an amount of 1 to 10% by weight of the protein dry matter present.

4. A food and/or feedstuff composition for humans or animals comprising protein from said composition replaced by at least one keto acid of a non-essential amino acid according to the formula R—CO—COOX, wherein R is a part of a non-essential amino acid and X is selected from the group consisting of hydrogen, an alkali metal, an alkaline earth metal or an organic base, wherein said keto acid is present in an amount of 1 to 20% by weight, which composition is capable of substantially reducing nitrogen excretion.

5. The composition of claim 4, wherein said keto acid is selected from alpha ketoglutaric acid, pyruvic acid and oxaloacetate.

6. The composition of claim 5, wherein said keto acid is alpha ketoglutaric acid.

7. The composition of claim 6, wherein said keto acids are present in the form of an acid and/or salt of alkali metal, alkaline earth metal or organic base.

8. The composition of claim 5, wherein said keto acids are pyruvic acid and alpha ketoglutaric acid.

9. The composition of claim 8, wherein said keto acids are present in the form of an acid and/or salt of alkali metal, alkaline earth metal or organic base.

10. The composition of claim 5, wherein said keto acid is oxaloacetate.

11. The composition of claim 10, wherein said keto acids are present in the form of an acid and/or salt of alkali metal, alkaline earth metal or organic base.

12. The composition of claim 5, wherein said keto acids are oxaloacetate and alpha ketoglutaric acid.

13. The composition of claim 12, wherein said keto acids are present in the form of an acid and/or salt of alkali metal, alkaline earth metal or organic base.

14. The composition of claim 5, wherein said keto acids are oxaloacetate and pyruvic acid.

15. The composition of claim 14, wherein said keto acids are present in the form of an acid and/or salt of alkali metal, alkaline earth metal or organic base.

16. The composition of claim 5, wherein said keto acids are present in the form of an acid and/or salt of alkali metal, alkaline earth metal or organic base.

17. The composition of claim 4, wherein said keto acid is present in an amount of 1 to 10% by weight.

18. The composition of claim 17, wherein said keto acids are present in the form of an acid and/or salt of alkali metal, alkaline earth metal or organic base.

19. The composition according to claim 4, wherein said protein has been replaced by two keto acids which are mixed in a weight relationship of 25:75 to 75:25.

20. The composition of claim 19, wherein said keto acids are present in the form of an acid and/or salt of alkali metal, alkaline earth metal or organic base.

21. The composition of claim 4, wherein said protein has been replaced by two keto acids which are mixed in a weight relationship of 40:60 to 60:40.

22. The composition of claim 21, wherein said keto acids are present in the form of an acid and/or salt of alkali metal, alkaline earth metal or organic base.

23. The composition of claim 4, wherein said keto acids are present in the form of an acid and/or salt of alkali metal, alkaline earth metal or organic base.

* * * * *